United States Patent [19]

Schell et al.

[11] 4,098,662

[45] Jul. 4, 1978

[54] CORROSION PROBE FOR USE IN MEASURING CORROSION RATE UNDER SPECIFIED HEAT TRANSFER CONDITIONS

[75] Inventors: Charles E. Schell, Levittown; Dennis C. Deegan, Glenside; Donald F. Jacques, Cornwells Heights, all of Pa.

[73] Assignee: Betz Laboratories, Inc., Trevose, Pa.

[21] Appl. No.: 644,201

[22] Filed: Dec. 24, 1975

[51] Int. Cl.² ........................................... G01N 27/46
[52] U.S. Cl. ............................... 204/195 C; 73/15 R; 73/112; 165/11
[58] Field of Search ............. 204/1 C, 195 C; 73/112, 73/15 R

[56] References Cited

U.S. PATENT DOCUMENTS

| | | | |
|---|---|---|---|
| 2,924,972 | 2/1960 | Bierman | 73/204 |
| 3,068,693 | 12/1962 | Perran et al. | 73/204 |
| 3,071,520 | 1/1963 | Smalling | 202/160 |
| 3,436,320 | 4/1969 | Marsh | 204/195 C |
| 3,716,460 | 2/1973 | Weisstuch et al. | 204/195 C |
| 3,788,962 | 1/1974 | Frenck | 204/195 C |
| 3,878,064 | 4/1975 | Weisstuch et al. | 204/195 C |
| 3,913,378 | 10/1975 | Hausler | 73/15 R |
| 3,918,300 | 11/1975 | Weisstuch et al. | 73/15 R |

OTHER PUBLICATIONS

Kent, "Corrosion", vol. 16, 1960, pp. 523t–529t.
Ailor, "Handbook on Corrosion Testing and Evaluation", 1971, pp. 732–740.

Primary Examiner—T. Tung
Attorney, Agent, or Firm—Alexander D. Ricci; Steven H. Markowitz

[57] ABSTRACT

A corrosion probe assembly for use in measuring corrosion and deposition rates for test specimens in corrodant electrolyte solutions is disclosed. The probe is designed for versatility, simplicity of construction, and serviceability and comprises a heated (hot) test specimen and, preferably, an unheated (cold) test specimen. Thus, the effects of heat load on the corrosion rates and on the deposition rates on various metallic surfaces can be readily determined. By sensing the inside temperature of the hot test specimen and the corrodant temperature, the heat transfer coefficient across the hot test specimen can readily be measured.

11 Claims, 6 Drawing Figures

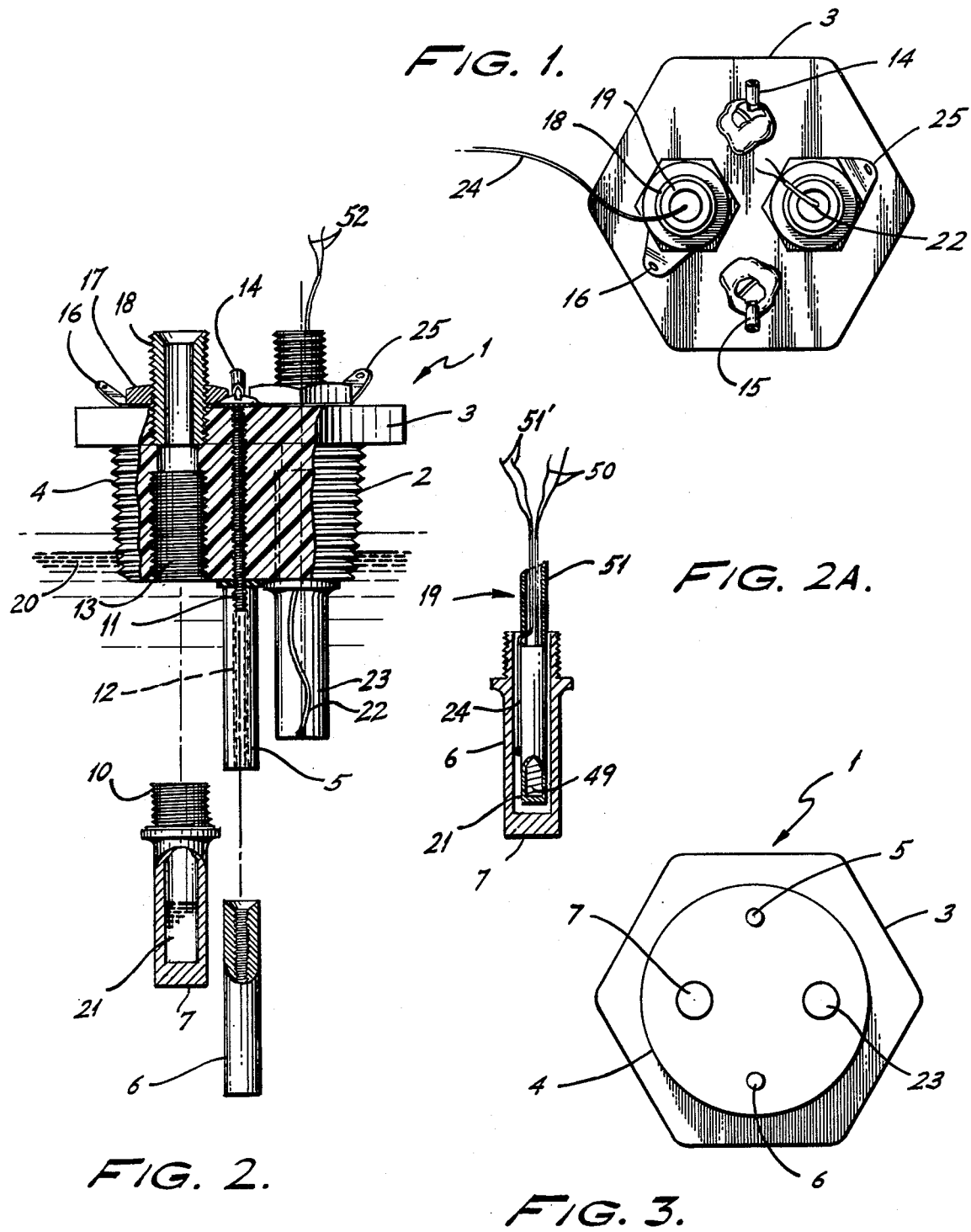

CORROSION PROBE FOR USE IN MEASURING CORROSION RATE UNDER SPECIFIED HEAT TRANSFER CONDITIONS

BACKGROUND OF THE INVENTION

The present invention relates to a corrosion probe used in both polarization and weight loss measurements of corrosion rates of metallic material upon exposure to a corrodant electrolyte.

Initially, corrosion rates were determined by simply inspecting the surfaces of corroded equipment. Such a method is undesirable since the equipment is often irreparably damaged before corrosion is evident. Furthermore, it is often necessary to shut-down equipment in order to make an inspection.

Accordingly, small test specimens were developed for relatively simple insertion and removal from a representative part of a corroding system to be tested. Typically, such test specimens are integral parts of a corrosion probe assembly which additionally includes support equipment for the specimens. These probe assemblies are designed for ease of incorporation into the test system. For example, the assembly may be designed as a pipe fitting, requiring no special tools for insertion techniques.

Two types of corrosion probe assemblies commonly used are known as weight loss types and polarization resistance types. Measurement of corrosion rate by weight loss probe assemblies is performed by initially measuring and recording the test specimen's initial weight to give $W_i$ (grams). The probe assembly is installed in the corrodant system such that the specimen is subjected to the system fluid, such as cooling water. The time of installation is recorded. At the end of the test period the specimen is removed and carefully cleaned in order to remove all corrosion products without removing uncorroded specimen material. Also, the time of specimen removal is recorded. The test specimen's final weight is measured to give $W_f$ (grams). The corrosion rate is calculated from this data from:

$$\text{Corrosion rate (mpy)} = K(W_i - W_f)/t \qquad (1)$$

where $t$ = time duration of the test (days) and $K$ = constant factor related to the metal being tested, its density, and its surface area.

Polarization type probe assemblies make use of the electrochemical nature of corrosion. Such probes typically utilize test, reference, and auxiliary electrodes. The test electrode, in the form of a test specimen, in initially permitted to corrode freely. A small electric current is passed through the corrodant between the test and auxiliary electrodes while the polarization potential between the test and reference electrodes is measured. The current is increased until a small given change in electrode potential, usually 10 mv, is measured between the test and reference electrodes. The resulting current required to produce the change is proportional to the instantaneous corrosion rate. Accordingly, this resultant current can be read and converted into units of corrosion rate. In fact, one among the inventors, in U.S. Pat. No. 3,716,460, which is hereby incorporated by reference, discloses a device which gives direct readings of instantaneous corrosion rate from a polarization-type probe assembly.

There is a third type of corrosion probe commonly used based on a measurement of electrical resistance of a small wire preferably manufactured from the same metal as in the test system. As the wire corrodes, its resistance increases since the diameter gets smaller. Thus, the change of resistance with time is a measure of the corrosion rate of the wire. The main disadvantage is that localized corrosion (pitting, deposit corrosion, etc.) has a tendency to cause the wire to corrode in a small area. Thus, the resistance measured will be determined largely by the smaller diameter which exists at the localized corrosion site. Also, since this site corrodes much faster than the rest of the wire, there is a tendency for the wire to break off at this point. The prime advantage of this technique is its ability to measure metallic corrosion in nonelectrolyte systems.

It is a common observation among workers in this field that there is often a discrepancy between hot corrosion and scaling occurring on surfaces experiencing heat transfer (e.g., heat exchanger surfaces) and cold corrosion and scaling occurring on those not experiencing heat transfer (e.g., corrosion specimens). Accordingly, the inventors set out to develop means for accurate corrosion rate measurements either by polarization resistance or by weight loss techniques wherein heat transfer is simultaneously taking place.

While conducting this developmental work, the inventors demonstrated that an interrelationship exists between the heat transfer coefficient (U) and corrosion and scaling in a system. As deposition increases it was observed that U is reduced. Also, corrosion products can contribute to the amount of deposition. In addition, reduced flow rate of the system fluid reduces U. It thus occurred to the inventors that a determination of heat transfer coefficient (U) in a corrodant system wherein corrosion and/or deposition occurs would provide an additional important tool in evaluating the system. In U.S. Patent application Ser. No. 430,453, filed on Jan. 3, 1974, now U.S. Pat. No. 3,918,300, which is hereby incorporated by reference, a U-meter is disclosed which provides an instantaneous U reading in a heat transfer system.

The probe assembly of the present invention permits detection of the necessary corrodant system parameters and feeding of the detected parameters into the U-meter for an instantaneous read-out of U. A test electrode or a test specimen of the probe assembly is heated, preferably electrically heated. The power W (watts), can be directly converted into heat, Q (BTU/hour), from the following relation:

$$Q = 3{,}413 \, W \qquad (2)$$

The heat flux (Q/A) is, then, $$\text{flux} = Q/A = 3.413 \, W/A \qquad (3)$$

where $A$ = test material specimen surface area. If, for example, the test material surface area is 9 cm² the flux would be as follows:

$$\text{flux (BTU/hr} - \text{ft}^2) = 352.3 \, W \text{ (watts)} \qquad (4)$$

If 10,000 BTU/hr − ft² (a reasonably high amount of heat flux in any plant heat exchanger) where needed in the probe assembly, then from equation (4), 28.4 watts should be fed to the heater.

At a fixed flow rate, U is defined by the equation:

$$Q/A = U(T_2 - T_1) \qquad (5)$$

where $Q$, $A$ and $U$ have been previously described; $T_2$ = temperature of test material surface (°F); $T_1$ = external fluid temperature (°F). Thus, $$U = (Q/A)/(T_2 - T_1) \qquad (6)$$

All that is now necessary to determine U is measurement of $T_2$ and $T_1$. This can be accomplished, for example, by placing a temperature probe in the fluid stream near the heat transfer surface to determine $T_1$ and placing a temperature sensor within the test specimen to determine $T_2$. It should be noted from equation (6) that, at constant $Q/A$ (constant $W$), $T_2 - T_1$ is sufficient to completely define U. Thus, the direct measurement of $T_2 - T_1$ is sufficient to determine the heat transfer coefficient.

During their work, the inventors discovered yet another important tool in evaluating corrodant systems and the treatment thereof. By simultaneously measuring cold corrosion and hot corrosion, the effect of the heat transfer load on the corrodant system can be determined. This can be accomplished by providing the probe assembly of the present invention with both a hot test specimen and a cold test specimen.

In fact, by providing a probe assembly with plural test sepcimens, various and sundry tests can be run to evaluate a corrodant system treatment program. For example, the simultaneous effect of heat load and different metallic materials in a corrodant system could be readily examined. Also, for example, galvanic interaction between two specimens can be studied by electrically connecting them externally and measuring current flowing between them.

Accordingly, it is an object of the present invention to provide a novel corrosion probe assembly which is very versatile in evaluating a corrodant system treatment program.

It is a further object of the present invention to provide a corrosion probe assembly which facilitates measurement of corrosion rate under specified heat transfer conditions.

Yet a further object of the present invention is to provide a corrosion probe which facilitates measurement of heat transfer coefficient simultaneously with measurement of corrosion rate.

An additional object of the present invention is to provide a corrosion probe which facilitates simultaneous measurement of hot and cold corrosion.

These and other objects, features and advantages of the present invention will become more apparent from the following description when taken in connection with the accompanying drawings which show, for purposes of illustration only, a preferred embodiment in accordance with the present invention and wherein:

FIG. 1 is a top plan view of a preferred embodiment of the invention;

FIG. 2 is a side elevational view of the probe assembly shown in FIG. 1 with a portion of the probe body broken away;

FIG. 2A is a detailed view of a part of the probe assembly shown in FIG. 2;

FIG. 3 is a bottom plan view of the probe assembly shown in FIG. 1;

Figure 4:
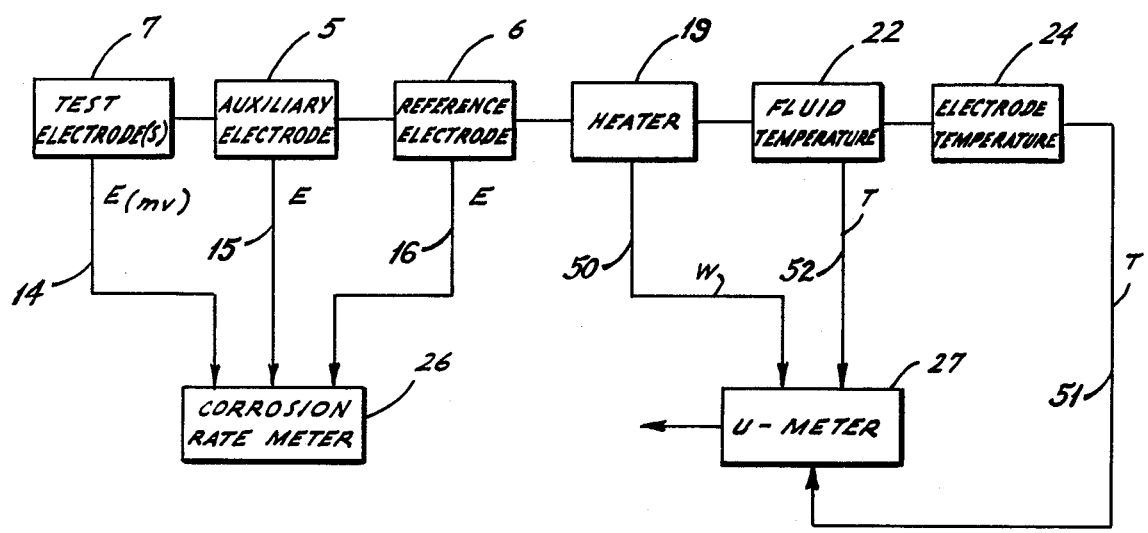
FIG. 4 is a block diagram illustrating the operation of the probe assembly of the present invention in conjunction with a corrosion rate meter and a U-meter.

Referring now to the drawings wherein like reference numerals are used throughout the various views to designate like parts, and more particularly to FIGS. 1 - 3, wherein the details of a probe with heat transfer are shown, the probe 1 comprises housing 2 having an upper polygonal portion 3 and a lower threaded portion 4. The threaded portion may typically be of 1 ½ inches NPT thread suitable for screwing the probe 1 into a standard pipe section (phantom lines in FIG. 2) through which the corrodant fluid is passed. The probe housing or body 2 may be fabricated from any nonconductive material which has suitable mechanical and chemical properties for the specific corrodant being tested. For example, a housing of PVC (polyvinyl chloride) has proven to be satisfactory for typical cooling water systems. The upper portion 3 of the housing is preferably hex shaped to accommodate the use of a tool, e.g., a wrench, for easy manipulation of the probe during insertion into or removal from the corrodant system.

The lower portion of the probe includes auxiliary electrode 5, reference electrode 6 and a test electrode 7.

Auxiliary electrode 5 is shown as a cylindrical rod which is attached to the bottom end of a threaded screw 11 at the bottom of housing 2. Electrical connector 14 is provided at the upper portion 3 of the housing and is conductively connected to electrode 5 by threaded screw 11. The auxiliary electrode is formed from a non-corrosive metal as in the reference electrode. For example, a stainless steel auxiliary electrode can be used together with a copper reference electrode and a mild steel test electrode.

Reference electrode 6 is also connected to housing 2 by the bottom end of a threaded screw (not shown in FIG. 2). The threaded screw conductively connects the reference electrode with electrical connector 15.

Test electrode 7 typically comprises the same material as the corroding surfaces in the corrodant system. The test electrode is hollowed inside and is provided with a threaded upper male connection 10. A threaded channel 13 extends through housing 2 and a protrusion upwardly of the housing forms a threaded upper nipple 18. The hollow test electrode is screw-connected to the lower end of channel 13 via threaded male connection 10. Element 16 is an electrical connector secured to nipple 18 by a hex nut 17. To simulate a specified heat transfer condition, electric heater 19 is inserted into the channel which is formed, conjointly, by upper nipple 18, channel 13, male connection 10 and the hollow test electrode 7. The hollow electrode 7 is filled with heat transfer fluid 21.

The U value, as outlined above, is known as the overall U and is comprised of two main parts - the U between the heat transfer fluid 21 and the metal electrode 7 and the U between the metal electrode and the corrodant fluid 20. To assist in determining the latter U, means for eliminating or minimizing the former component is provided. The simplest way of doing this is to fill hollow test electrode 7 with a heat transfer fluid 21 which has a thermal conductivity similar to that of the electrode. This is accomplished if the fluid is a liquid metal such as gallium, mercury or Wood's metal. This latter component of U is further broken down into two components:

(1) a constant component (if flow rate is constant). Its properties relate specifically to the character of the corrodant fluid/metal interface. (2) a variable component which is the one of interest. Its properties relate to scaling, corrosion, etc. as discussed earlier.

The specified heat load should be evenly distributed over the surface of test electrode 7. This can be accomplished by using a helically would heating element 49 which extends very closely to the bottom of electrode 7 and stops very close to the top of the electrode. Element 51 is an upper cylindrical extension of the heating element 49. The numeral 50 indicates electrical wires connected to the heating element 49.

$T_1$ is measured using temperature sensing probe 22 which is placed in the corrodant fluid near the heat transfer surface of electrode 7. This can be accomplished through an arrangement similar to the test electrode mounting arrangement. Probe 22 is placed inside metal cylinder 23 so that intimate contact is made with the walls of the cylinder.

Measurement of $T_2$ is accomplished by inserting temperature sensing probe 24 into hollow electrode 7 such that the lower end thereof is submersed in heat transfer fluid 21. One advantage of the liquid metal heat transfer fluid 21 is that the temperature thereof should be very close to the temperature of electrode 7 and, thus, very close to $T_2$. Any temperature sensing arrangement compatible with the geometry of the corrosion probe can be used in practicing the present invention.

Figure 5:
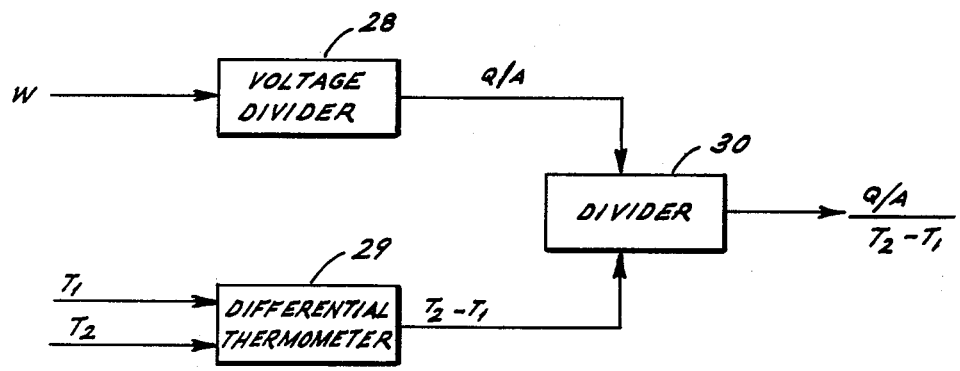
FIG. 5 is a block diagram showing detailed operation of the U-meter shown in FIG. 4.

The connection of the various corrosion probe elements with the above-noted U-meter of U.S. patent application Ser. No. 430,453 filed Jan. 3, 1974, and the above-noted corrosion rate meter of U.S. Pat. No. 3,716,460 is shown in FIG. 4 The test electrode 7, auxiliary electrode 5 and reference electrode 6 are electrically connected, via electrical connections 14-16, to corrosion rate meter 26 in a manner clearly taught in the noted patent. Heater 19 and temperature sensing probes 22 and 24 are connected to U-meter 27 by wires 50, 51 and 52. FIG. 5 is a block diagram, corresponding to FIG. 5 of the noted patent application, showing a slight modification of the U-meter of the noted patent application which is necessary for operation with the probe assembly of the present invention. Instead of using two differential thermometers which feed results into a divider, the present corrosion probe assembly requires a voltage divider 28 and a differential thermometer 29 which feed results into divider 30. Heater 19 is electrically connected to voltage divider 28 for feeding W (watts) thereto. The voltage divider 28 is set according to equation (3) to send Q/A to divider 30. Temperature sensing probes 22 and 24 send $T_1$ and $T_2$ to differential thermometer 29. Accordingly, the differential thermometer feeds $T_2 - T_1$ to divider 30. Divider 30, in turn, will give U from equation (6). Also, as noted earlier, if W is maintained constant, $T_2$ and $T_1$ measurements can be used to determine U values.

Accordingly, the above-described corrosion probe assembly can be used to evaluate a corrodant fluid system, for example as follows:

The probe assembly 1, which is connected to a U-meter, is inserted into the corrodant system of interest, e.g., cooling water, process fluid, boiler water, etc., so that the corrodant fluid is in contact with the specimens or electrodes and flows past them at a predetermined rate. The test metal specimen or electrode 7 has been filled with heat transfer fluid 21. After the probe assembly is inserted into the corrodant system, the heater 19 is inserted. To begin heat transfer, the heater is provided with electrical power from either an adjustable A.C. source or an adjustable D.C. source. If the corrosion rate is being measured by polarization resistance using a corrosion rate meter, periodic values of corrosion rate and U are recorded over the test period. If the corrosion rate is being measured by weight loss, periodic readings are of U are recorded with corrosion rate being determined as already outlined above. It should readily occur to the artisan, having the benefit of the present disclosure, that if a comparison between hot corrosion and cold corrosion is desired, a test specimen or test electrode is used as cyliner 23, or if the effect of hot corrosion on different test metals is desired, this can be accomplished by using a test specimen or electrode 23 of a different metal than specimen or electrode 7 and heating specimen or electrode 23. Thus, it can be seen that the probe assembly of the present invention is extremely versatile in evaluating a corrodant fluid system.

Although the invention has been described in way of the preferred embodiment, it is understood that the description is by way of illustration only, and it is contemplated that modifications and variations may be made by those skilled in the art without departing from the spirit of the invention.

We claim:

1. An assembly for measuring corrosion rate under specified heat transfer conditions, said assembly comprising:
    corrosion probe housing means for insertion into a conduit through which corrodant fluid flows,
    a plurality of corrosion rate meter electrodes located on said housing means for exposure to said corrodant fluid, said electrodes comprising a reference electrode, an auxiliary electrode, and a first hollow test electrode, said test electrode containing heat transfer fluid with a heat transfer coefficient similar to that of the test electrode,
    electrical heating means located within said first hollow test electrode for heating an inside wall surface thereof, said heating means having an electrical input and being at least partially submersed in said heat transfer fluid,
    first temperature sensing means located inside said first hollow test electrode between said heating means and said inside wall surface, said first temperature sensing means being submersed in said heat transfer fluid for sensing the temperature of said fluid,
    second temperature sensing means for sensing the temperature of the corrodant fluid adjacent an outside wall surface of the test electrode,
    corrosion rate meter means conductively connected to said reference, auxiliary and first test electrodes for instantaneously measuring the corrosion rate of said first test electrode, and
    heat transfer coefficient meter means conductively connected to said electrical heating means input and said first and second temperature sensing means for instantaneously measuring the heat transfer coefficient across a wall of said first test electrode.

2. An assembly according to claim 1, additionally having a fourth corrosion rate meter electrode.

3. An assembly according to claim 2, wherein said fourth electrode is a cold corrosion rate meter test electrode.

4. An assembly according to claim 3, wherein said second temperature sensing means is provided in said fourth electrode.

5. An assembly according to claim 3, wherein said hot and cold test electrodes are made of different materials.

6. An assembly according to claim 1, wherein a second test electrode is provided also heated by heating means is provided.

7. An assembly according to claim 6, wherein said first and second heated test electrodes are made of different materials.

8. A device for measuring corrosion rate according to claim 1, wherein said electrode means are all connected to one end of said corrosion probe housing means.

9. An assembly according to claim 8, wherein said heat transfer fluid is non-flowing.

10. An assembly according to claim 1, wherein said test electrode is closed at one end.

11. An assembly according to claim 1, wherein said heat transfer fluid is non-flowing.

* * * * *

UNITED STATES PATENT OFFICE
CERTIFICATE OF CORRECTION

Patent No. 4,098,662                    Dated July 4, 1978

Inventor(s) Charles E. Schell, Dennis C. Deegan, Donald F. Jacques

It is certified that error appears in the above-identified patent and that said Letters Patent are hereby corrected as shown below:

Column 1, line 51, change "in" (second occurrence) to --- is ---.
Column 2, line 49, change "3,413" to --- 3.413 ---.
Column 3, line 26, change "sepcimens" to --- specimens ---.

Signed and Sealed this

Fourteenth Day of November 1978

[SEAL]

Attest:

RUTH C. MASON
Attesting Officer

DONALD W. BANNER
Commissioner of Patents and Trademarks